US00PP26075P3

(12) United States Plant Patent
Rákosi

(10) Patent No.: US PP26,075 P3
(45) Date of Patent: Nov. 10, 2015

(54) ***ECHINACEA* PLANT NAMED 'FOURTH OF JULY'**

(50) Latin Name: *Echinacea purpurea*
Varietal Denomination: Fourth of July

(71) Applicant: Adorján Rákosi, Csemo (HU)

(72) Inventor: Adorján Rákosi, Csemo (HU)

( * ) Notice: Subject to any disclaimer, the term of this patent is extended or adjusted under 35 U.S.C. 154(b) by 175 days.

(21) Appl. No.: 13/998,413

(22) Filed: Oct. 30, 2013

(65) Prior Publication Data

US 2015/0121594 P1 Apr. 30, 2015

(51) Int. Cl.
*A01H 5/02* (2006.01)

(52) U.S. Cl.
USPC ..... Plt./428

(58) Field of Classification Search
USPC ..... Plt./428
See application file for complete search history.

*Primary Examiner* — Anne Grunberg
(74) *Attorney, Agent, or Firm* — James M. Weatherly; Barbara Campbell; Cochran Freund & Young, LLC

(57) ABSTRACT

A new *Echinacea* plant particularly distinguished by having an upright growth habit, large number of ray florets, and a yellow-green stem color is disclosed.

2 Drawing Sheets

Genus and species: *Echinacea purpurea.*
Variety denomination: 'Fourth of July'.

BACKGROUND OF THE NEW PLANT

The present invention comprises a new and distinct variety of coneflower, botanically known as *Echinacea purpurea*, and hereinafter referred to by the variety name 'Fourth of July'. 'Fourth of July' originated from an open pollination between an unknown female *Echinacea purpurea* plant and an unknown male *Echinacea purpurea* plant in Csemö, Hungary in the summer of 2005. 'Fourth of July' was first propagated in Csemö, Hungary. 'Fourth of July' was found to reproduce true to type in successive generations of asexual propagation via division in Csemö, Hungary.

CROSS REFERENCE TO RELATED APPLICATIONS

Plant Breeder's Rights for 'Fourth of July' were applied for in Europe on Jul. 18, 2013, Application No. 2013/1969. 'Fourth of July' has not been made publicly available or sold more than one year prior to the filing date of this application.

SUMMARY

The following are the most outstanding and distinguishing characteristics of this new variety when grown under normal horticultural practices in Gouda, the Netherlands.

1. Upright growth habit;
2. Large number of ray florets; and
3. A yellow-green stem color.

DESCRIPTION OF THE PHOTOGRAPHS

This new *Echinacea* plant is illustrated by the accompanying photographs. The photographs are of a plant 9 months from planting grown in an open field in Gouda, the Netherlands in August of 2013. The colors shown are as true as can be reasonably obtained by conventional photographic procedures.

DESCRIPTION OF THE NEW VARIETY

Figure 1:
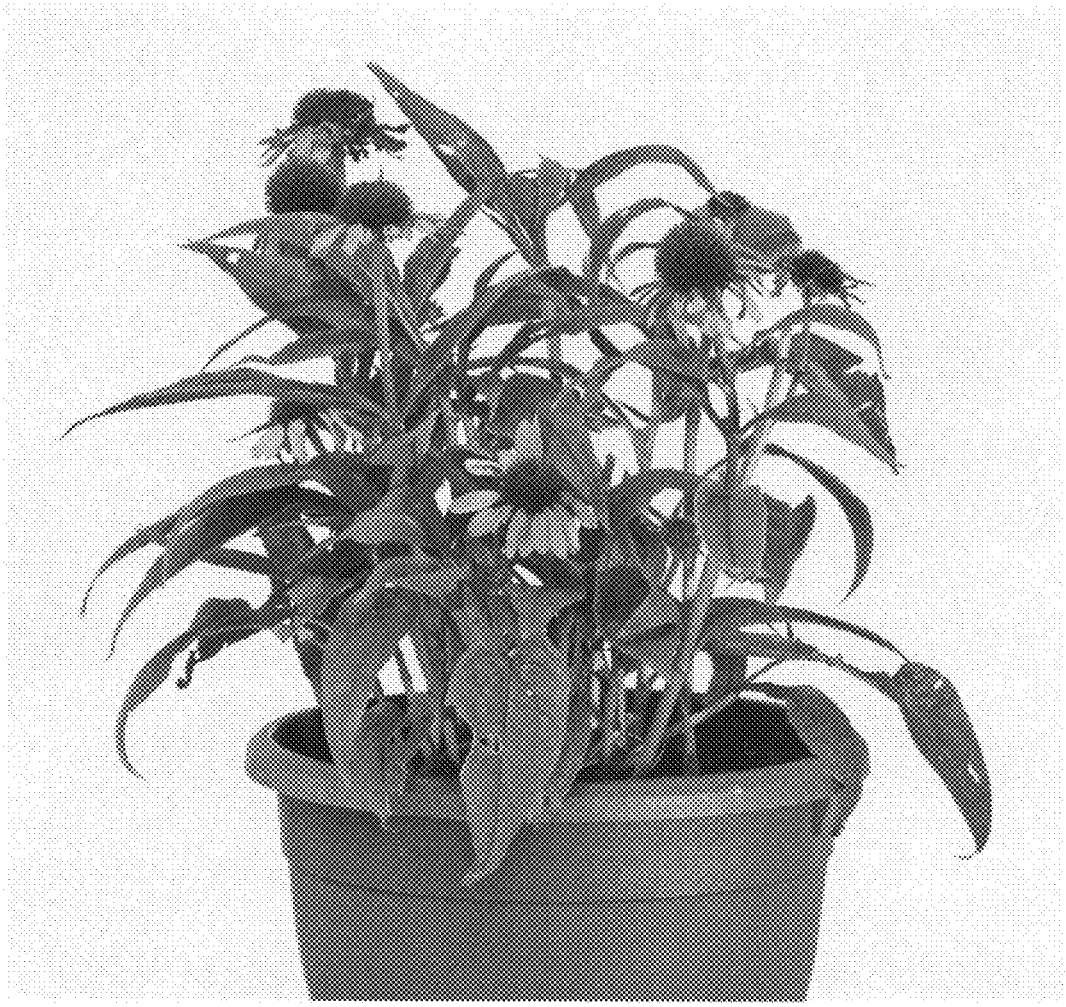
FIG. 1 shows the overall plant habit of the plant grown in a pot.
Figure 2:
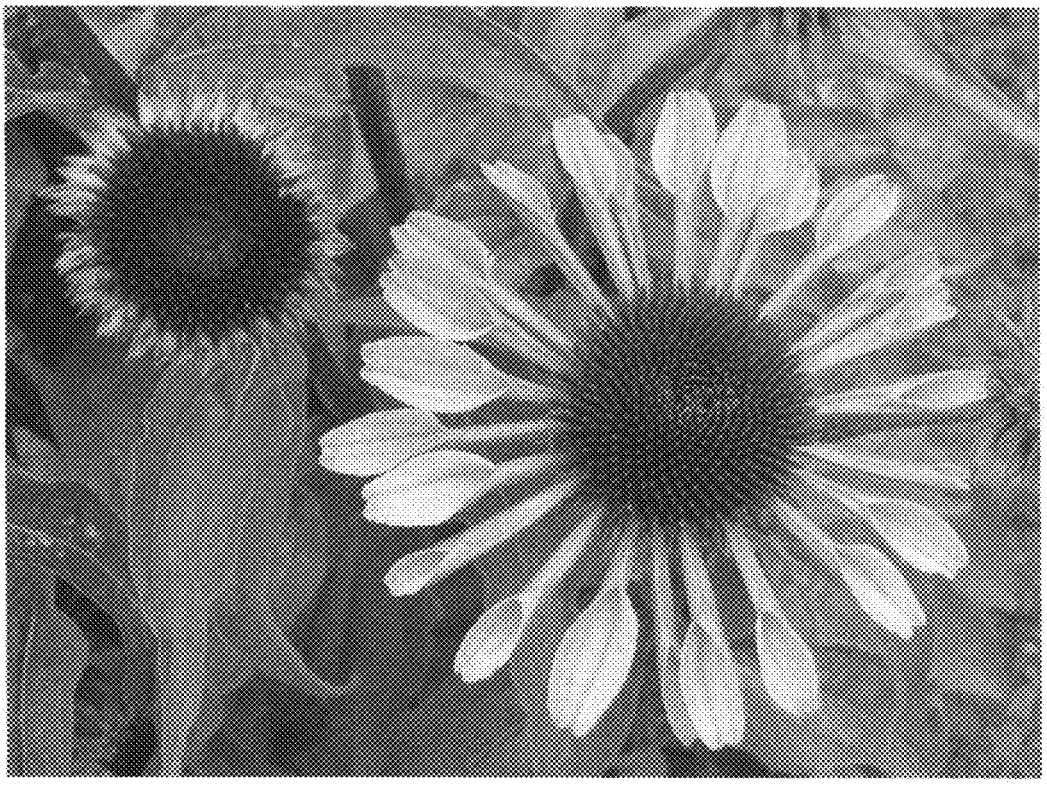
FIG. 2 shows a close-up of a mature flower of the plant.
Figure 3:
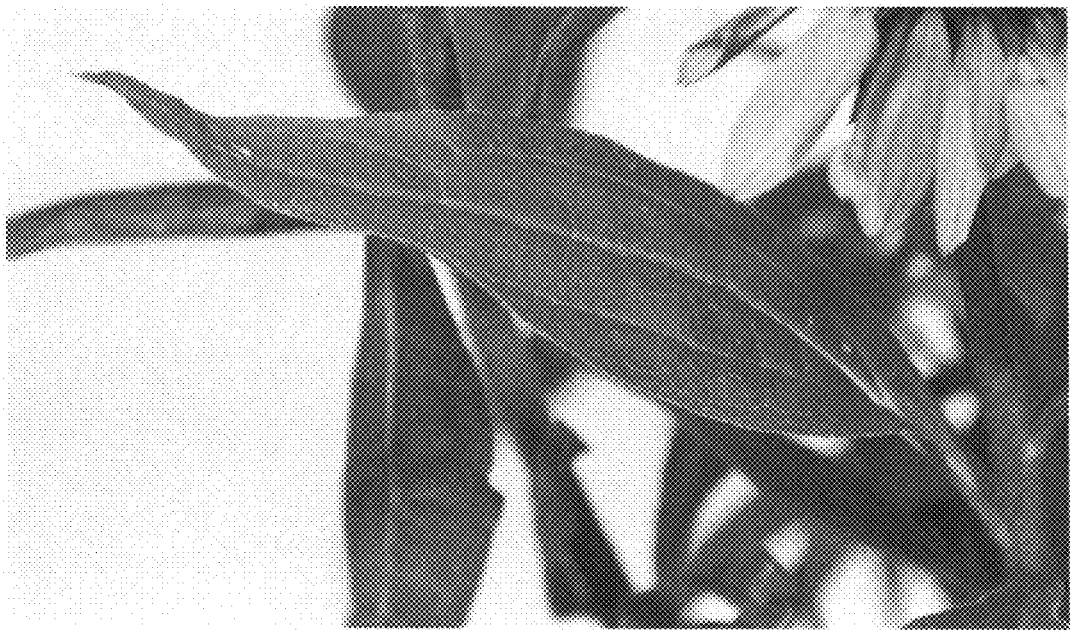
FIG. 3 shows a close-up of a mature leaf of the plant.

The following detailed descriptions set forth the distinctive characteristics of 'Fourth of July'. The data which define these characteristics were collected in Gouda, the Netherlands in August, 2013. Data was collected on three year old field grown plants with a day temperature of 18° C. to 32° C. and a night temperature of 8° C. to 20° C. Color references are to The R.H.S. Colour Chart of The Royal Horticultural Society of London (R.H.S.), 7$^{th}$ edition (2007).

Classification:
- *Family.*—Asteraceae.
- *Species.*—*Echinacea purpurea.*
- *Common name.*—Coneflower.
- *Variety.*—'Fourth of July'.

Parentage:
- *Female.*—Unknown female *Echinacea purpurea.*
- *Male.*—Unknown male *Echinacea purpurea.*

Plant description:
- *Plant form.*—Herbaceous perennial.
- *Growth habit.*—Upright.
- *Flowering habit.*—Continuously from early July to late September.
- *Natural flowering season.*—Summer, early July to late September.
- *Time to flower.*—9 months.
- *Time to produce flowering plant.*—9 months.
- *Shape.*—Broad, obovate.
- *Plant height.*—31.7 cm.
- *Plant diameter.*—38.4 cm.
- *Growth rate.*—Approximately 7.0 cm per month (in the Spring).

*Vigor*.—Slow to moderate.
*Branching habit*.—Main flowering stems grow from the base with basal branching.
*Appropriate containers or cropping system*.—Field grown or in pots.

Lateral branches:
*Number*.—18 main stems.
*Length*.—18.8 cm.
*Diameter*.—0.5 cm.
*Internode length*.—5.4 cm.
*Appearance*.—Rounded, rough to the touch due to the presence of short strigose hairs.
*Aspect*.—80° from base.
*Strength*.—Strong.
*Color*.—RHS 144A (Yellow-green).
*Pubescence*.—Stems covered with short, strigose hairs. Length: 0.05 cm. Color: RHS NN155D (White).

Foliage description:
*Arrangement*.—Alternate, simple.
*Length*.—14.1 cm.
*Width*.—3.9 cm.
*Shape*.—Narrow, ovate.
*Apex*.—Acute.
*Base*.—Attenuate.
*Margin*.—Entire to shallowly serrated.
*Pubescence*.—Upper and lower surfaces: Moderately covered with very short strigose hairs. Length: 0.03 cm. Color: Closest to RHS NN155D (White).
*Venation pattern*.—Pinnate.
*Color*.—Developing leaves: Upper surface: From RHS N137A (Green) to RHS 147A (Yellow-green). Lower surface: RHS 147B (Yellow-green). Mature leaves: Upper surface: From RHS N137A (Green) to RHS 147A (Yellow-green). Lower surface: RHS 147B (Yellow-green).
*Venation*.—Upper surface: RHS 145D (Yellow-green). Lower surface: RHS 145B (Yellow-green).

Petioles:
*General*.—Upper stem leaves nearly sessile.
*Length*.—0.3 cm.
*Width*.—0.2 cm.
*Shape*.—V-shaped.
*Texture*.—Upper surface: Smooth. Lower surface: Smooth, margins sparsely covered with very short strigose hairs, average length 0.03 cm, color RHS NN155D (White).
*Color*.—Upper surface: RHS N137A (Green). Lower surface: RHS 144B (Yellow-green), with margins RHS 137A (Green).

Inflorescence:
*Type*.—Persistent, terminal capitulum consisting of ray florets and disc florets.
*Aspect*.—Straight on top of main stems and lateral stems.
*Inflorescence height*.—3.0 cm.
*Inflorescence diameter*.—6.6 cm.
*Disc diameter*.—3.3 cm.
*Quantity of open inflorescences per lateral stem*.—2.
*Quantity of buds per lateral stem*.—1.
*Quantity of open inflorescences and buds per plant*.—54.
*Rate of inflorescence opening*.—Main (terminal) inflorescence opens first, followed by the secondary inflorescence.
*Longevity of inflorescence on plant*.—A few weeks.
*Fragrance*.—Absent.

Bud:
*Length*.—1.5 cm.
*Diameter*.—1.8 cm.
*Shape*.—Flattened globular.
*Color*.—RHS 200A (Brown).

Receptacle:
*Shape*.—Ovate.
*Height*.—1.0 cm.
*Diameter*.—0.8 cm.
*Color*.—RHS 155C (White).

Ray florets:
*Arrangement*.—Rotate.
*Number per inflorescence*.—20.
*Row of ray florets*.—1.
*Appearance*.—Smooth, upper surface dull, under side slightly glossy.
*Aspect*.—Nearly horizontal, but slightly dropping to an average angle of 30° downward.
*Shape*.—Oblanceolate.
*Apex*.—Emarginate to undeeply cleft.
*Base*.—Tubular.
*Margin*.—Entire.
*Length*.—2.9 cm.
*Width*.—0.9 cm.
*Texture*.—Upper surface: Smooth, carinate (slightly ribbed lengthways). Lower surface: Smooth, slightly glossy, carinate (moderately ribbed lengthways).
*Color*.—When opening: Upper surface: RHS 186A (Greyed-purple), tube is RHS 59A (Red-purple). Lower surface: RHS 183A (Greyed-purple), tube is RHS 173D (Greyed-orange), tinged with RHS 59B (Red-purple) to RHS 59C (Red-purple). Mature: Upper surface: RHS 70B (Red-purple), tube is darker RHS 59A (Red-purple). Lower surface: RHS 185C (Greyed-purple), tube is RHS 182C (Greyed-red) to RHS 182D (Greyed-red). Fading: Upper surface: RHS 186B (Greyed-purple), tube is RHS 187B (Greyed-red) to RHS 187C (Greyed-red). Lower surface: RHS 146D (Yellow-green).

Disc florets:
*Appearance*.—Tubular; smooth, glossy.
*Arrangement*.—Spirally placed on disc.
*Number of disc florets per inflorescence*.—Approximately 250.
*Shape*.—Tubular, upper 20% free.
*Apex*.—Acute.
*Base*.—Fused into tube.
*Margin*.—Entire.
*Length*.—0.5 cm.
*Width*.—0.2 cm.
*Texture*.—Upper and lower surface: Smooth, glossy.
*Color*.—When opening: Upper and lower surface: RHS 144A (Yellow-green), free tips and mid-section. Mature: Upper and lower surface: Free tips and mid-section is RHS 178A (Greyed-red), with base RHS 144A (Yellow-green).

Involucral bracts:
*Appearance*.—Dull.
*Arrangement*.—Spirally placed in three rows.
*Number of involucral bracts per inflorescence*.—60.
*Number of rows of bracts*.—3.
*Shape*.—Ovate to narrow ovate.
*Apex*.—Acute.
*Base*.—Cuneate.

*Margin*.—Entire.
*Length*.—0.9 cm.
*Width*.—0.3 cm.
*Texture*.—Upper side: Smooth. Lower surface: Margins moderately to densely covered with very short hairs, average length is 0.05 cm, color close to RHS NN155D (White).
*Color*.—Upper surface: RHS N137A (Green). Lower surface: RHS N137D (Green).

Receptacle spines:
*Number of spines per disc floret*.—Approximately 250.
*Shape*.—Acicular.
*Apex*.—Acute.
*Base*.—Attenuate.
*Texture*.—Smooth, glossy.
*Color*.—Apex: RHS 53A (Red). Mid-section: RHS 143A (Green). Base: RHS 143B (Green).

Peduncle:
*Length*.—6.5 cm from uppermost leaf to base of inflorescence.
*Diameter*.—0.5 cm.
*Aspect*.—Straight on top of main (flowering) stem, average angle of secondary peduncles 20°.
*Strength*.—Strong.
*Texture*.—Moderately covered with very short strigose hairs, average length is 0.03 cm with a color of RHS NN155D (White).
*Color*.—RHS 144A (Yellow-green).

Reproductive organs:
*Stamen number*.—5.
*Filament length*.—0.3 cm.
*Filament color*.—RHS 145A (Yellow-green).
*Anther shape*.—Linear.
*Anther length*.—0.025 cm.
*Anther color*.—RHS 200A (Brown).
*Pollen amount*.—Moderate.
*Pollen color*.—RHS 15B (Yellow-orange).
*Pistil number*.—1.
*Pistil length*.—0.7 cm.
*Stigma shape*.—Unequal decurrent.
*Stigma color*.—RHS 183A (Greyed-purple).
*Style length*.—0.55 cm.
*Style color*.—RHS 145A (Yellow-green).
*Ovary color*.—RHS 145D (Yellow-green).

Fruits/seeds: Fruit and seed development have not been observed.

Disease/pest resistance: Not more susceptible to pests or disease than other *Echinacea purpurea* varieties.

Tolerance to wind: Moderate.

Tolerance to rain: Moderate.

Tolerance to heat: At least tolerant to temperatures up to 35° C.

Tolerance to cold: USDA zones 3 to 4.

COMPARISON WITH KNOWN VARIETY

'Fourth of July' is a distinct variety of *Echinacea* and is most similar to the *Echinacea* plant named 'All that Jazz' (U.S. Plant Pat. No. 21,771). Differences between the two varieties are described in Table 1:

TABLE 1

Comparison with Similar Variety

| Trait | Variety 'Fourth of July' | Commercial line 'All that Jazz' |
|---|---|---|
| Plant Shape | Shorter and stronger than 'All that Jazz' | Relatively looser and taller than 'Fourth of July' |
| Number of ray florets | Greater than 'All that Jazz' | Less than 'Fourth of July' |
| Stem color | Yellow-green | Green |

I claim:

1. A new and distinct variety of *Echinacea* plant named 'Fourth of July' as illustrated and described herein.

* * * * *